United States Patent
Wagner et al.

(10) Patent No.: US 6,244,740 B1
(45) Date of Patent: Jun. 12, 2001

(54) MIXER FOR MULTI-COMPONENT PASTES, INCORPORATING A DELAY CHAMBER

(75) Inventors: Ingo Wagner, Herrsching; Gerd Brandhorst, Landsberg; Marc Peuker, Seefeld; Christina Wolf, Munich, all of (DE)

(73) Assignee: Espe Dental AG, Seefeld (DE)

( * ) Notice: Subject to any disclaimer, the term of this patent is extended or adjusted under 35 U.S.C. 154(b) by 0 days.

(21) Appl. No.: 09/413,637

(22) Filed: Oct. 6, 1999

(30) Foreign Application Priority Data

Oct. 16, 1998 (DE) .......................................... 298 18 499 U

(51) Int. Cl.7 ....................................................... B01F 5/06
(52) U.S. Cl. ..................... 366/181.5; 366/336; 222/145.6
(58) Field of Search ..................................... 366/336, 339, 366/340, 181.5; 222/145.5, 145.6, 135–137, 459

(56) References Cited

U.S. PATENT DOCUMENTS

| | | | |
|---|---|---|---|
| 2,816,518 | * | 12/1957 | Daggett . |
| 3,570,719 | * | 3/1971 | Schiff ..................................... 222/137 |
| 4,408,890 | * | 10/1983 | Beckmann ........................... 366/339 |
| 4,538,920 | * | 9/1985 | Drake .................................... 366/339 |
| 4,767,026 | * | 8/1988 | Keller et al. . |
| 4,771,919 | * | 9/1988 | Ernst . |
| 4,995,540 | * | 2/1991 | Colin et al. ........................... 222/137 |
| 5,033,650 | * | 7/1991 | Colin et al. ........................... 222/137 |
| 5,080,262 | * | 1/1992 | Herold et al. . |
| 5,186,363 | * | 2/1993 | Haynes . |
| 5,249,709 | * | 10/1993 | Duckworth et al. .................. 222/137 |
| 5,249,862 | * | 10/1993 | Herold et al. . |
| 5,421,650 | * | 6/1995 | Meyer . |
| 5,487,606 | * | 1/1996 | Keller . |
| 5,498,078 | * | 3/1996 | Keller . |

FOREIGN PATENT DOCUMENTS 0 302 819 A2   8/1989  (EP) .

* cited by examiner

Primary Examiner—Charles E. Cooley
(74) Attorney, Agent, or Firm—Connolly Bove Lodge & Hutz LLP

(57) ABSTRACT

A mixer is used for producing multi-component pastes at a mixing ratio other than 1:1. A deviating channel 20 is provided between the inlet opening 16 for the component of the larger volume proportion and the mixing chamber, to delay the feed of this component with respect to the other component. The presence of this deviating channel 20 causes all components to enter the mixing chamber simultaneously, thereby obtaining a paste which has the desired mixing ratio from the start.

3 Claims, 1 Drawing Sheet

MIXER FOR MULTI-COMPONENT PASTES, INCORPORATING A DELAY CHAMBER

BACKGROUND OF THE INVENTION

Pasty multi-component masses, such as dental impression masses, are produced by means of mixing devices in which the individual components of the mass are simultaneously supplied from separate cartridge cylinders to a mixer which dispenses the mixed paste from a front end. The mixer may be a static mixer or a dynamic mixer (having a rotary mixer element). The paste exiting from the front end of the mixer may be supplied directly onto an impression spoon.

Depending on the viscosity and mixing ratio, the fact that the pressure builds up differently in the individual cartridge cylinders at the start of the device may cause the components to reach the mixer at different times. In such a case, the first length of paste exiting from the mixer has a mixing ratio which differs from a desired value and may therefore cure less perfectly or more slowly, or have other undesired properties.

In case one of the components is a base paste and the other is a catalyst of a dental impression mass, a typical mixing ratio of base paste to catalyst is 5:1. Due to the different properties and/or amounts of material and the differently sized inlet openings of the mixer, it can be observed that the mixing chamber is filled with the base paste before the catalyst arrives, so that a first length of approximately 3 cm of the final paste fails to have the desired mixing ratio.

Known is a static mixer for producing pastes from different amounts of components, which includes a housing having at its rear end an inlet opening for each component. A space provided between a mixing chamber and a plate, which has the inlet openings for the two components, is divided into two chambers by a partition wall extending in the axial direction of the mixer. One of the chambers forms a straight axial flow path for the component of the smaller volume proportion, whereas the other chamber covers the remaining cross-sectional area, which is substantially larger than the volume proportion of this component, and which is separated from the mixing chamber by a transverse wall. This other chamber thus forms a retaining volume which is filled by the component of the larger volume proportion before that component can pass a narrow passage provided in the transverse wall and reaching the mixer element. This is intended to ensure that the two different components reach the mixing chamber substantially simultaneously.

A problem exiting with this known device resides in the fact that the above-mentioned transverse wall with the narrow passage increases the flow resistance for the respective component considerably, thus rendering the overall device sluggish. As another disadvantage, the axial length of the device is significantly increased by the retaining space.

EP 0 302 819 A2 discloses a cartridge magazine for a flowable mass comprising two containers of different diameters for receiving different amounts of two components of the mass. Due to the fact that a common outlet pipe is offset from the axial center toward one edge of the cartridge system, the connecting channels between the cartridge outlets and the common outlet pipe have different lengths. In this known mixer, the above-mentioned problem of an improper mixing ratio at the beginning occurs at the second and each further application when there is no longer a time difference in time in the advancement of the components.

SUMMARY OF THE INVENTION

It is an object of the invention to provide a mixer for producing multicomponent pastes, which is as smooth to operate and compact as possible and which permits the production of a pasty mixture that has a desired mixing ratio from the start.

To this end, a mixer for producing a paste by mixing nonequal amounts of components in accordance with the present invention comprises a housing having a longitudinal axis, a rear end provided with separate inlet openings for each component, and a front end provided with a dispensing opening, a mixing chamber formed in the housing, and a delay chamber formed in the housing between one of the inlet openings and the mixer chamber, the delay chamber extending along an arc about the longitudinal axis so as to increase the length of the path to be followed by the component applied to the one inlet opening. The deviation channel may have the same cross-section throughout its length as the corresponding inlet opening so that the overall flow resistance is hardly increased. Moreover, the deviation channel is so disposed that it does not substantially increase the overall dimensions of the mixer.

In a preferred embodiment of the invention, the mixer is a dynamic mixer, with a mixer element provided in the mixing chamber and supported in the housing for rotation about the longitudinal axis.

For producing pastes from two components, it is preferred that the positions at which the components enter the mixing chamber are offset from each other by less than 180° about the longitudinal axis. This is specifically advantageous because both components are supplied to the mixer element at closely adjacent positions, thus rendering each mixing process effective from the start.

In an embodiment of a mixer for producing dental impression masses from a base substance and a catalyst substance, the deviating channel is preferably disposed between the inlet opening passed by the base substance and the mixing chamber. This structure is useful for typical base-catalyst substances. Moreover, since a certain excess of catalyst only results in slightly faster curing without substantially altering the properties of the final paste, the structure advantageously ensures that the mixing chamber is first wetted by the catalyst to produce a paste that is properly mixed from the start.

DETAILED DESCRIPTION OF A PREFERRED EMBODIMENT

Figure 1:
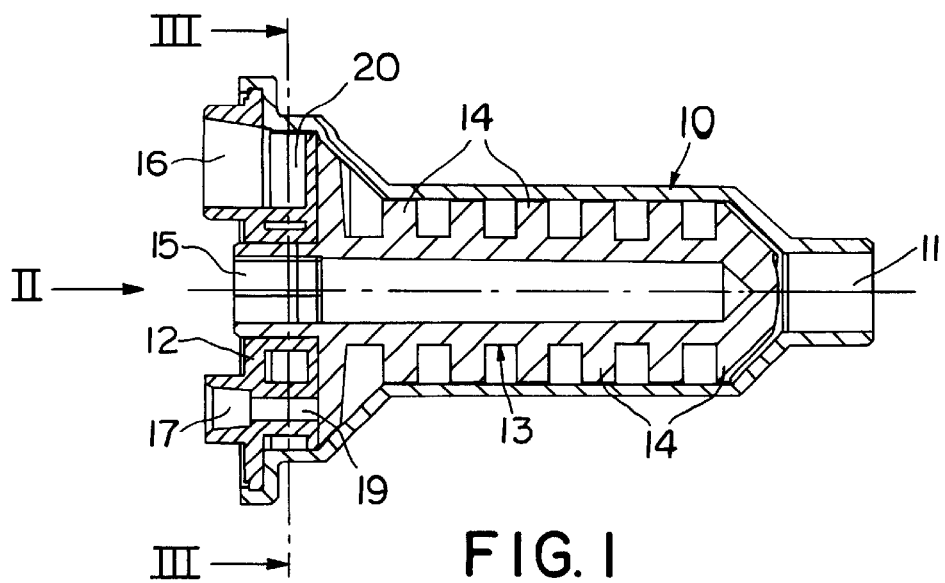
FIG. 1 is an axial section through a mixer taken along the line I—I of FIG. 2.
Figure 2:
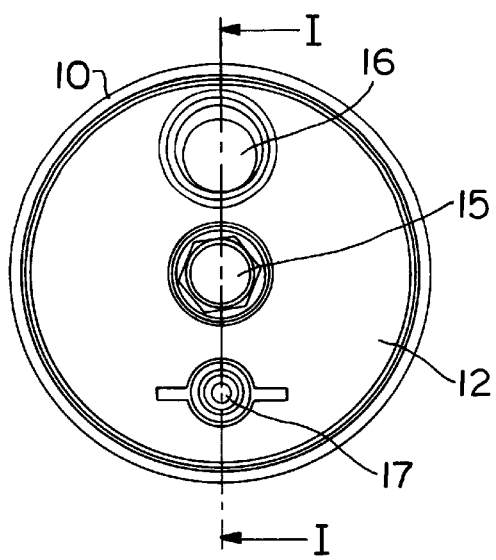
FIG. 2 is a front view of the mixer seen in the direction of the arrow II in FIG. 1.

The mixer shown in the drawing includes a housing 10 which has a cylindrical mixing chamber and a front dispensing opening 11, a terminating plate 12 forming the rear wall of the housing 10, and a mixer element 13 supported by the terminating plate 12 and including mixing vanes 14. A hexagonal opening 15 is provided at the rear end of the mixer element 13 for coupling to a drive shaft (not shown).

The terminating plate 12 has two rearward extending inlet pipes 16, 17 by which the mixer may coupled to the front end of a cartridge placed in a dispensing apparatus (not shown). In the embodiment illustrated, the mixer is assumed to be adapted for producing a dental impression mass which is mixed from a pasty base substance and a catalyst substance at a ratio of, e.g., 5:1. To this end, the inlet pipe 16 for the base substance has a cross-sectional area that is five times the cross-sectional area of the inlet pipe 17 for the catalyst.

Figure 3:
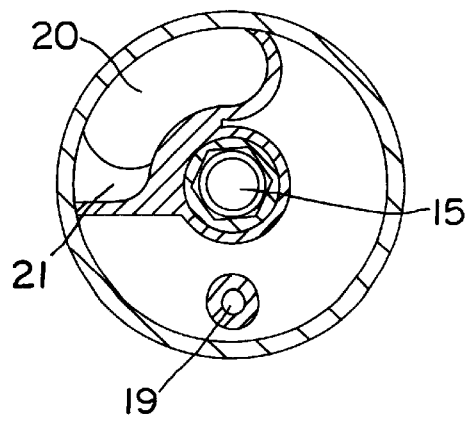
FIG. 3 is a section taken along the line III—III in FIG. 1.

As appears from FIGS. 1 and 3, a channel 19 connected to the inlet pipe 17 leads straight into the mixing chamber containing the mixer element 13.

On the other hand, the path followed by the base substance extends from the inlet pipe 16 to the mixing chamber via a deviating channel 20 and a passage 21 disposed at the end of the channel 20. The deviating channel 20 extends in a plane which is substantially transverse of the longitudinal axis of the mixer, and in the example shown extends along an arc covering an angle of about 90° about the axis of the mixer. This plane may be inclined with respect to the axis thereby resulting in a somewhat helical overall shape of the deviating channel 20.

The deviating channel 20 connected to the inlet pipe 16 has the effect that the passage 21 is offset from the straight inlet pipe 17 by less than 180°, thereby causing the two components to reach the mixing chamber at closely adjacent positions. This is of advantage for a thorough mixing.

When the mixer is started, the dispensing apparatus (not shown) presses the two components into the inlet pipes 16 and 17 by means of pistons provided in the cartridge cylinders. While the catalyst supplied through the inlet pipe 17 reaches the mixing chamber immediately via the axially extending straight channel 19, the base substance supplied to the inlet pipe 16 flows to the mixing chamber via the deviating channel 20 and the passage 21. As result, the base substance, which is the component of the larger volume proportion, reaches the mixing chamber at least not prior to the catalyst.

If the catalyst reaches the mixing element 13 sufficiently early to wet the mixing element before the arrival of the base substance, this may change the initial mixing ratio; in the dental impression mass assumed, however, a slight excess of catalyst is uncritical and preferred to an excess of base substance.

For other materials, the flow relations may be different from those assumed above. If the components are, e.g., materials of similar flow properties, it is possible that the component passing through the narrower inlet pipe 17 is pressurized to a greater degree due to the smaller cross-section and is thus ejected faster. In such a case, it may be necessary to provide a deviating channel similar to the channel 20 behind the narrower inlet pipe 17 rather than behind the wider inlet pipe 16.

The measures described above are applicable also to mixers for producing a paste from more than two components. In such a case, deviating channels may be provided behind two or more inlet pipes and/or have different lengths to ensure that, depending on the flow properties of each component, all components reach the mixing element 13 substantially simultaneously.

What is claimed is:

1. A mixer for producing a paste by mixing non-equal amounts of components, said mixer comprising:

(a) a housing having a longitudinal axis, a rear end provided with separate inlet openings for each of said components, and a front end provided with a dispensing opening;

(b) a mixing chamber formed in said housing and having an entry side facing a rear end of said housing;

(c) flow paths extending from each of said inlet openings to said mixing chamber, each flow path having a length measured from the respective inlet opening to said mixing chamber entry side;

(d) a delay chamber formed in one of said flow paths, said delay chamber constituting a deviating channel extending in a plane substantially transverse to, and along an arc about, said longitudinal axis so as to increase the length of one flow path over the length of each other flow path upstream of said mixing chamber; and (e) a mixer element provided in said mixing chamber, said mixer element being supported in said housing for rotation about said longitudinal axis.

2. The mixer according to claim 1, for producing pastes from two components, wherein said flow paths are connected to said mixing chamber entry side at positions which are offset from each other by less than 180° about said longitudinal axis.

3. The mixer according to claim 1, for producing dental impression masses from a base substance and a catalyst substance, wherein said delay chamber is formed in the flow path passed by the base substance.

* * * * *